(12) United States Patent
Hohlbein

(10) Patent No.: US 10,076,180 B2
(45) Date of Patent: Sep. 18, 2018

(54) ORAL CARE IMPLEMENT

(71) Applicant: COLGATE-PALMOLIVE COMPANY, New York, NY (US)

(72) Inventor: Douglas Hohlbein, Hopewell, NJ (US)

(73) Assignee: Colgate-Palmolive Company, New York, NY (US)

( * ) Notice: Subject to any disclaimer, the term of this patent is extended or adjusted under 35 U.S.C. 154(b) by 447 days.

(21) Appl. No.: 14/650,803

(22) PCT Filed: Dec. 10, 2012

(86) PCT No.: PCT/US2012/068668
§ 371 (c)(1),
(2) Date: Jun. 9, 2015

(87) PCT Pub. No.: WO2014/092672
PCT Pub. Date: Jun. 19, 2014

(65) Prior Publication Data
US 2015/0313350 A1 Nov. 5, 2015

(51) Int. Cl.
| A46B 5/02 | (2006.01) |
| B65G 1/10 | (2006.01) |
| A61C 17/22 | (2006.01) |
| B25G 1/10 | (2006.01) |

(52) U.S. Cl.
CPC .............. *A46B 5/026* (2013.01); *A46B 5/02* (2013.01); *A46B 5/021* (2013.01); *A61C 17/225* (2013.01); *A46B 2200/1066* (2013.01); *B25G 1/102* (2013.01); *Y10T 16/476* (2015.01); *Y10T 16/498* (2015.01)

(58) Field of Classification Search
CPC ........... A46B 5/02; A46B 5/021; A46B 5/026; B25G 1/00; B25G 1/10; B25G 1/102; Y10T 16/476; Y10T 16/498
USPC .................................. 15/143.1; 16/430, 436
See application file for complete search history.

(56) References Cited

U.S. PATENT DOCUMENTS

| 2,094,240 A | 9/1937 | Herrick et al. |
| 2,179,266 A | 11/1939 | Lukenbill |
| 5,325,560 A | 7/1994 | Pavone et al. |

(Continued)

FOREIGN PATENT DOCUMENTS

| DE | 298 05 323 | 7/1999 |
| DE | 10 2005 055044 | 5/2007 |

(Continued)

OTHER PUBLICATIONS

Partial machine translation of DE 102005055044, May 24, 2007.*

(Continued)

*Primary Examiner* — Mark Spisich

(57) ABSTRACT

An oral care implement having a grip component. In one embodiment, the invention can be an oral care implement comprising: an elongated body comprising a head portion and a handle portion, the handle portion comprising a socket; at least one tooth cleaning element mounted to the head portion of the elongated body; and a first grip component comprising: an annular rim defining a central opening, the annular rim formed of a rigid material; and a resilient body mounted to the annular rim that covers the central opening, the resilient body formed of a resilient material; the first grip component mounted within the socket.

20 Claims, 13 Drawing Sheets

(56) References Cited

U.S. PATENT DOCUMENTS

| | | | |
|---|---|---|---|
| 5,713,104 A | 2/1998 | Giampaolo, Jr. | |
| 6,066,282 A | 5/2000 | Kramer | |
| 6,230,366 B1* | 5/2001 | Lin | A45C 13/26 16/431 |
| 6,464,920 B1 | 10/2002 | Kramer | |
| 6,687,940 B1* | 2/2004 | Gross | A46B 5/02 132/311 |
| 6,919,038 B2 | 7/2005 | Meyer et al. | |
| 7,039,984 B1 | 5/2006 | Watanabe et al. | |
| 7,047,591 B2 | 5/2006 | Hohlbein | |
| 7,118,364 B2 | 10/2006 | Morawski | |
| 7,241,413 B2 | 7/2007 | Pfenniger et al. | |
| 7,472,448 B2 | 1/2009 | Hohlbein et al. | |
| 2003/0172483 A1 | 9/2003 | Davis | |
| 2004/0117934 A1 | 6/2004 | Pfenniger et al. | |
| 2005/0066462 A1 | 3/2005 | Moskovich et al. | |
| 2006/0026784 A1 | 2/2006 | Moskovich et al. | |
| 2006/0080795 A1 | 4/2006 | Pfenniger et al. | |
| 2008/0244849 A1 | 10/2008 | Moskovich et al. | |
| 2009/0007369 A1 | 1/2009 | Hohlbein et al. | |
| 2009/0193604 A1 | 8/2009 | Pfenniger et al. | |
| 2011/0146015 A1 | 6/2011 | Moskovich et al. | |
| 2011/0167579 A1 | 7/2011 | Huber et al. | |

FOREIGN PATENT DOCUMENTS

| | | | |
|---|---|---|---|
| EP | 0 580 406 | | 1/1994 |
| JP | 2002-336049 | * | 11/2002 |
| JP | 2003-275027 | * | 9/2003 |
| WO | 96/10934 | * | 4/1996 |
| WO | WO 2000/64306 | | 11/2000 |
| WO | WO 2004/026162 | | 4/2004 |
| WO | WO 2005/063143 | | 7/2005 |

OTHER PUBLICATIONS

International Search Report and the Written Opinion of the International Searching Authority issued in International Patent Application PCT/US2012/068668 dated Sep. 17, 2013.

Written Opinion of the International Preliminary Examining Authority issued in International Patent Application PCT/US2012/068668 dated Feb. 19, 2015.

* cited by examiner

ORAL CARE IMPLEMENT

CROSS-REFERENCE TO RELATED PATENT APPLICATIONS

This application is a U.S. national stage application under 35 U.S.C. § 371 of PCT Application No. PCT/US2012/068668, filed Dec. 10, 2012, the entirety of which is incorporated herein by reference.

BACKGROUND OF THE INVENTION

Toothbrushes made of a single plastic material and toothbrushes made of two plastic components, which are produced for example by a two component injection molding process, are known. In the latter case, known toothbrushes generally comprise a first part made of a rigid plastic material and a second part made of a resilient plastic material. In such known toothbrushes, the rigid plastic and resilient plastic must be selected so that they bond with one another at the surface where the two plastic parts come into contact with one another. Thus, there are restrictions in the selection of the plastic materials, and consequently in the design of the toothbrush. As a result of these restrictions, the material selected for the resilient plastic part of the handle may not be as resilient as a user would desire because it is difficult to bond an extremely resilient plastic with a rigid plastic. Thus, a need exists for an improved oral care implement having a grip component.

BRIEF SUMMARY OF THE INVENTION

The present invention is directed to an oral care implement having an improved gripping region. In one aspect, the oral care implement includes a handle and a head. The handle includes a socket formed therein. An annular rim having a resilient body mounted thereto is secured in the socket.

In one embodiment, the invention can be an oral care implement comprising: an elongated body comprising a head portion and a handle portion, the handle portion comprising a socket; at least one tooth cleaning element mounted to the head portion of the elongated body; and a first grip component comprising: an annular rim defining a central opening, the annular rim formed of a rigid material; and a resilient body mounted to the annular rim that covers the central opening, the resilient body formed of a resilient material; the first grip component mounted within the socket.

In another embodiment, the invention can be an oral care implement comprising: a head having at least one tooth cleaning element; a handle coupled to the head, the handle comprising at least one through-hole extending through the handle, the through-hole terminating as a first opening on a first side of the handle and terminating as a second opening on a second side of the handle; a first grip component coupled to the handle to enclose the first opening, the first grip component comprising an annular rim defining a central opening and a first resilient body mounted to the annular rim that covers the central opening, the annular rim formed of a first material and the first resilient body formed of a second material; a second grip component coupled to the handle to enclose the second opening, the second grip component comprises a second resilient body formed of a third material.

In yet another embodiment, the invention can be a method of manufacturing an oral care implement comprising: a) forming, from a first material, an elongated body comprising a handle portion and a head portion, a socket formed into the handle portion; b) forming a first grip component comprising an annular rim having a central opening and a first resilient body mounted to the annular rim covering the central opening, the annular rim formed of a second material and the first resilient body formed of a third material; and c) mounting the first grip component to the handle portion within the socket; and wherein the first and second materials are rigid materials and the third material is a resilient material.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
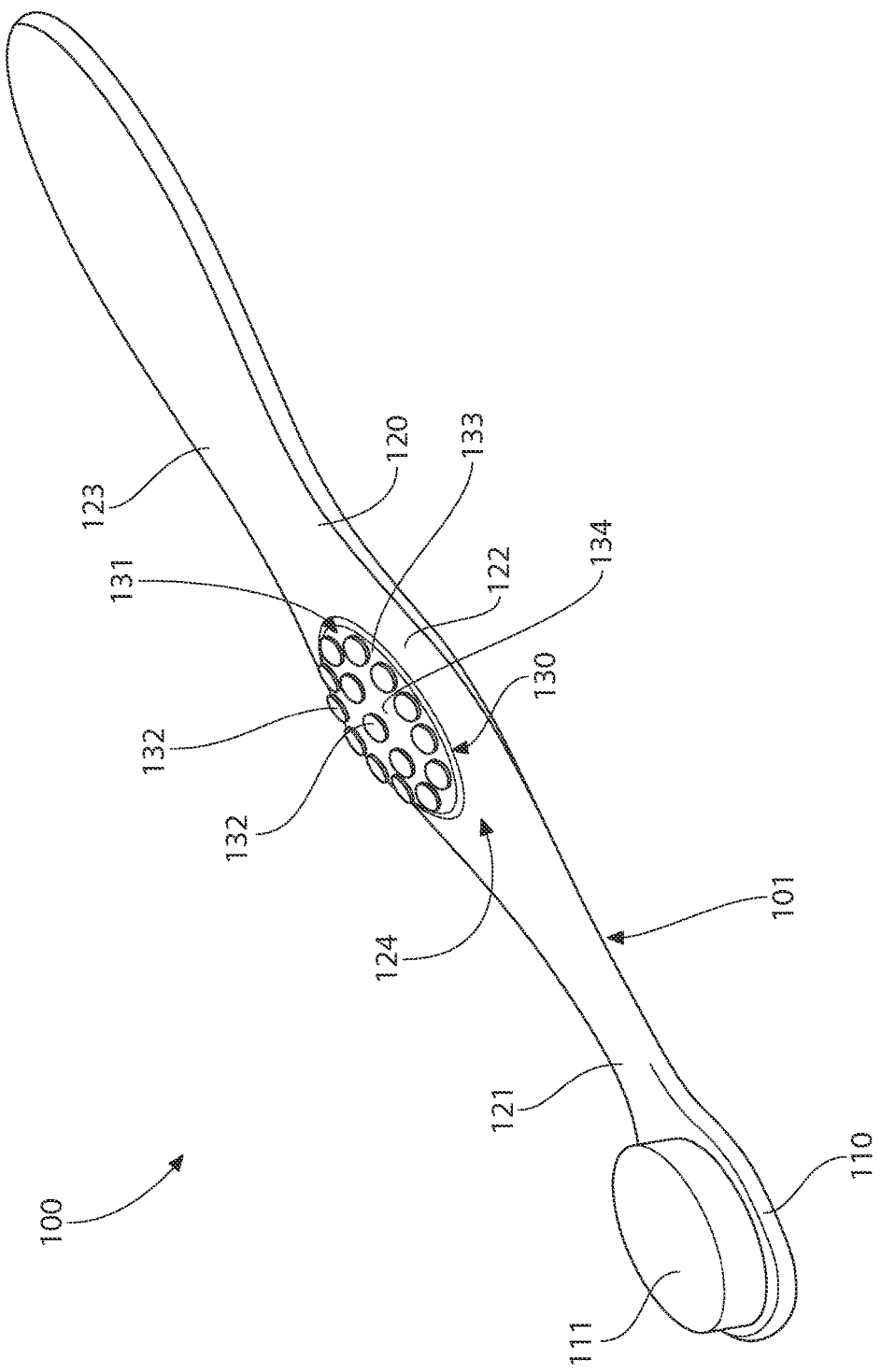
FIG. 1 is a perspective view of an oral care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
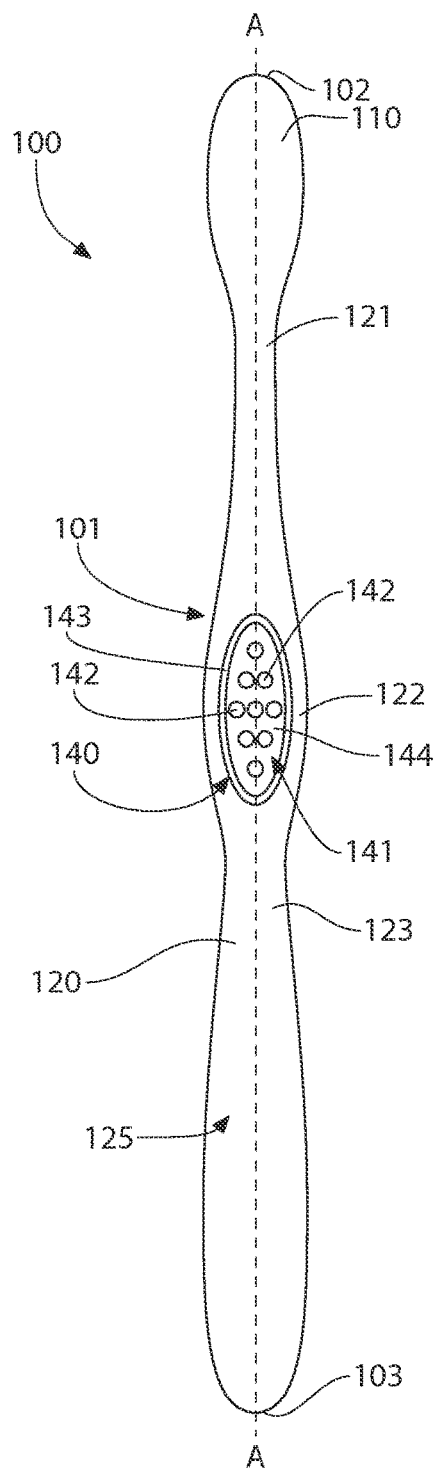
FIG. 2 is a rear view of the oral care implement of FIG. 1.
Figure 3:
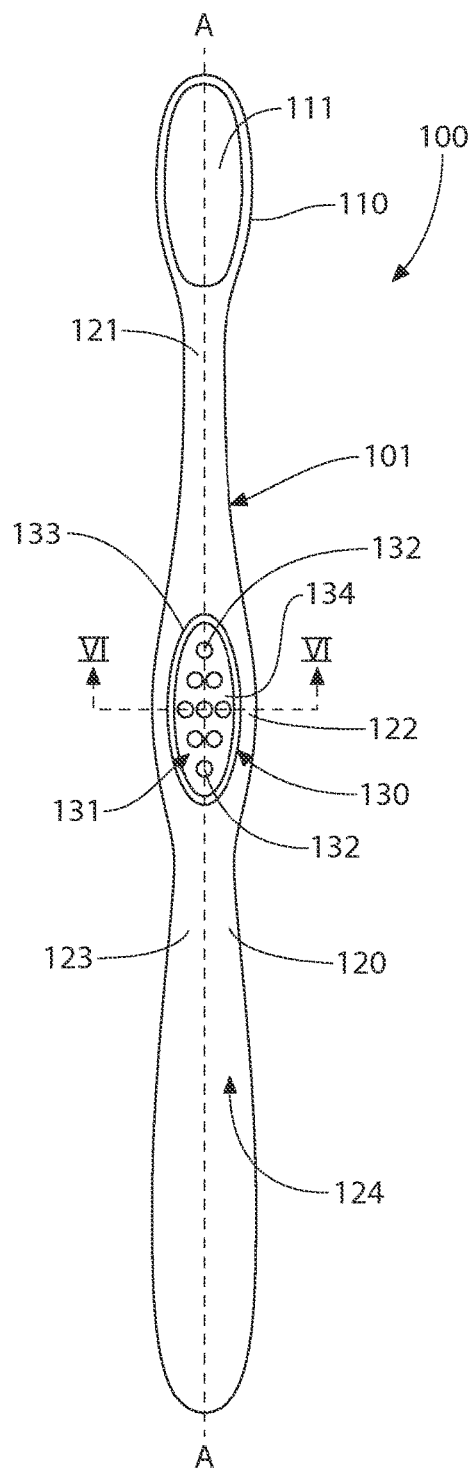
FIG. 3 is a front view of the oral care implement of FIG. 1.

Referring first to FIGS. 1-3 concurrently, an oral care implement 100 in accordance with an embodiment of the present invention will be described. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement extends from a proximal end 103 to a distal end 102 along a longitudinal axis A-A. The oral care implement 100 generally includes an elongated body 101 comprising a head portion 110 and a handle portion 120. The handle portion 120 is an elongated structure that provides the mechanism by which the user can hold and manipulate the oral care implement 100 during use. The handle portion 120 of the oral care implement 100 comprises a neck section 121, a thumb-grip section 122 and a finger grip section 123. The thumb-grip section 122 is located in between the neck section 121 and the finger grip section 123. Furthermore, the handle portion 120 comprises a front surface 124 and an opposing rear surface 125.

In the exemplified embodiment, the handle portion 120 is generically depicted having various contours for user comfort. More specifically, in the exemplified embodiment the thumb-grip section 122 of the handle portion 120 is the widest section of the handle portion 120. Specifically, the thumb-grip section 122 has a width that is greater than a width of the neck section 121 of the handle portion 120 and of the finger grip section 123 of the handle portion 120. Of course, the invention is not to be so limited in all embodiments and in certain other embodiments the thumb-grip section 122 may not have a greater width than the neck section 121 and the finger grip section 123. However, the handle portion 120 can take on a wide variety of shapes, contours and configurations, none of which are limiting of the present invention unless so specified in the claims.

In the exemplified embodiment, the handle portion 120 is formed of a rigid plastic material, such as for example without limitation polymers and copolymers of ethylene, propylene, butadiene, vinyl compounds and polyesters such as polyethylene terephthalate. Of course, the invention is not to be so limited in all embodiments and the handle portion 120 may be formed with a resilient material, such as a thermoplastic elastomer, over portions of or the entirety of the handle portion 120 to enhance the gripability of the handle portion 120 during use. For example, portions of the handle portion 120 that are typically gripped by a user's palm during use, such as the finger grip section 123 of the handle portion 120, may be overmolded with a thermoplastic elastomer or other resilient material to further increase comfort to a user.

The head portion 110 of the oral care implement 100 is coupled to the handle portion 120. In the exemplified embodiment, the head portion 110 of the oral care implement 100 is provided with a generic block that illustrates tooth cleaning elements 111 extending therefrom. The exact structure, pattern, orientation and material of the tooth cleaning elements 111 is not to be limiting of the present invention unless so specified in the claims. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 111 of the present invention can be connected to the head portion 110 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In certain embodiments, the head portion 110 may also include a soft tissue cleanser coupled to or positioned on its rear surface. An example of a suitable soft tissue cleaner that may be used with the present invention and positioned on the rear surface of the head portion 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

In the exemplified embodiment, the head portion 110 is formed integrally with the handle portion 120 as a single unitary structure using a molding, milling, machining or other suitable process. However, in other embodiments the handle portion 120 and the head portion 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

A first grip component 130 is coupled to the handle portion 120 in the thumb-grip section 122 of the handle portion 120 on the front surface 124 of the handle portion 120. Furthermore, a second grip component 140 is coupled the handle portion 120 in the thumb-grip section 122 of the handle portion 120 on the rear surface 125 of the handle portion 120. Although the invention is illustrated and described herein with the first grip portion 130 on the front surface 124 of the handle portion 120 and the second grip portion 140 on the rear surface 125 of the handle portion 120, the invention is not to be so limited and the first and second grip portions 130, 140 can be positioned opposite to that shown. Thus, in certain embodiments the front and rear surfaces 124, 125 may merely be first and second surfaces, without any specific correlation between front and rear. The first grip component 130 is separate and distinct from the second grip component 140 as will be discussed in more detail below.

The first grip component 130 has a front or outer surface 131 and a plurality of protuberances 132 protruding from the outer surface 131. Similarly, the second grip component 140 has a front or outer surface 141 and a plurality of protuberances 142 protruding from the outer surface 141. In the exemplified embodiment, the protuberances 132, 142 of the first and second grip components 130, 140 are in the shape of columnar projections extending from the outer surfaces 131, 141 of the first and second grip components 130, 140, respectively. However, the invention is not to be so limited in all embodiments and the protuberances 132, 142 can be in the form of nubs, elongate ridges, or combinations thereof. Furthermore, the exact number, size and shape of the protuberances 132, 142 are not to be limiting of the present invention in all embodiments unless claimed. In still other embodiments the protuberances 132, 142 can be omitted altogether and the outer surfaces 131, 141 of the first and second grip components 130, 140 can be smooth and free of protuberances.

In the embodiment exemplified in FIGS. 1-3, the first grip component 130 comprises an annular rim 133 and a first resilient body 134. Similarly, the second grip component 140 comprises an annular rim 143 and a second resilient body 144. In certain exemplified embodiments, each of the first and second resilient bodies 134, 144 is a resilient membrane. Furthermore, in the exemplified embodiments each of the first and second resilient bodies 134, 135 are free of penetrations. As will be discussed in more detail below, in certain embodiments only one of the first and second grip components 130, 140 includes the annular rim, and the other of the first and second grip components 130, 140 includes only a first resilient body 134.

Figure 4:
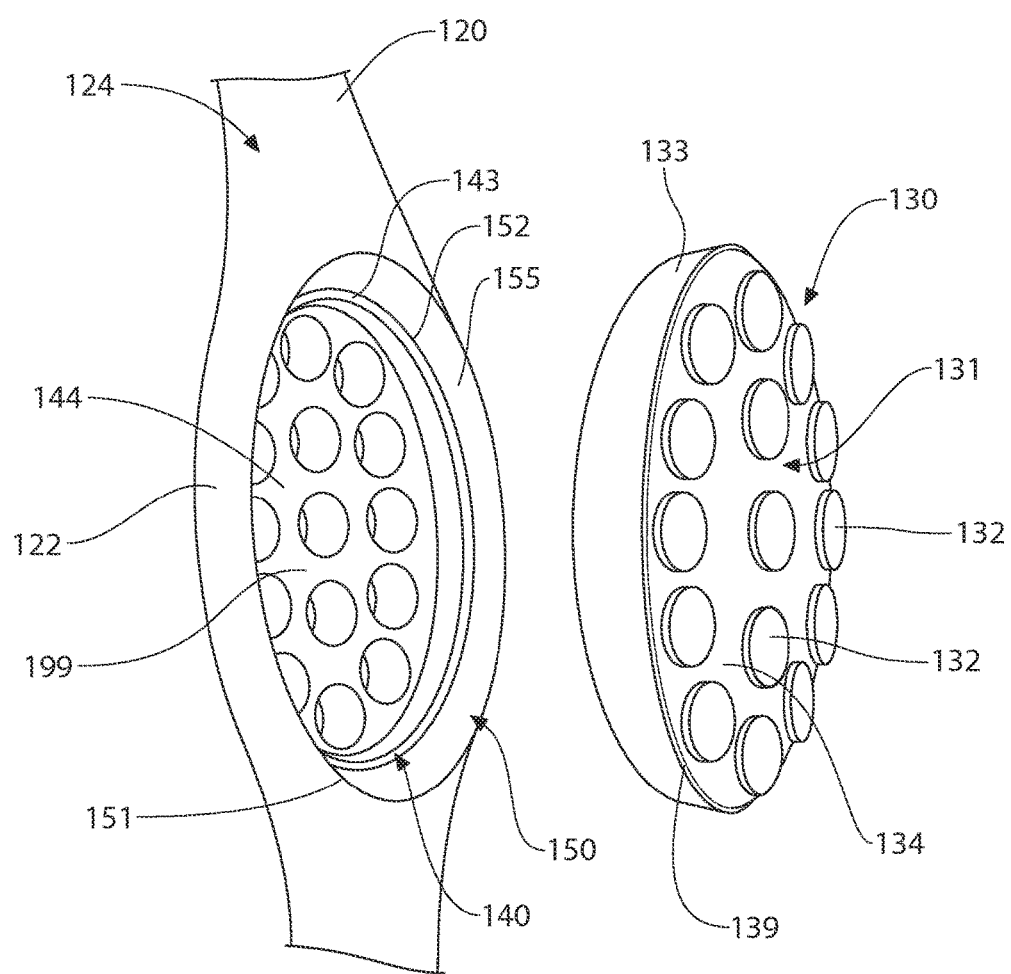
FIG. 4 is a close-up view of a portion of a handle of the oral care implement of FIG. 1 with a first grip component separated from the handle and a second grip component coupled to the handle.
Figure 5:
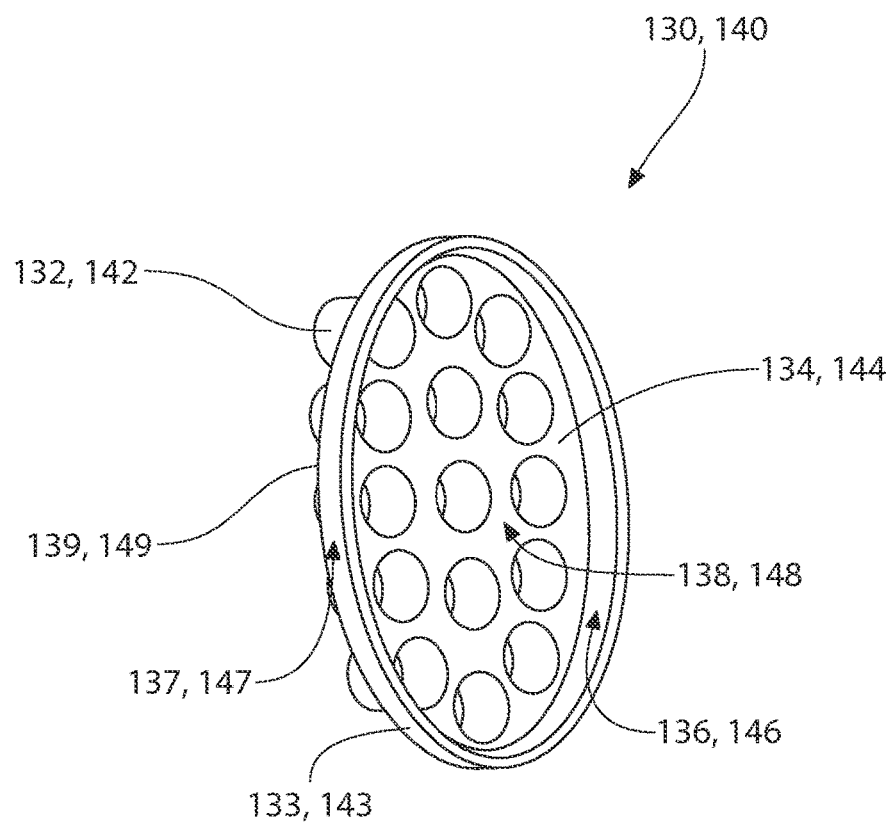
FIG. 5 is a perspective view of the first and second grip components of FIG. 4.

Referring now to FIGS. 4 and 5 concurrently, the first and second grip components 130, 140 will be further described. FIGS. 4 and 5 illustrate an embodiment whereby the first and second grip components 130, 140 have the same structure. Specifically, FIGS. 4 and 5 illustrate the first grip component 130 having the annular rim 133 and the first resilient body 134 and the second grip component 140 having the annular rim 143 and the second resilient body 144. In FIG. 4, the second grip component 140 is illustrated secured to the handle 120 and the first grip component 130 is separated from the handle 120. As noted above and as will be discussed in more detail below with reference to FIG. 7, in certain embodiments the first and second grip components 130, 140 may include different components. In certain instances in the description of FIGS. 4 and 5, the details of the first grip component 130 will be provided only, and it should be appreciated that the details are equally applicable to the second grip component 140.

The handle portion 120 comprises a socket 199 formed therein. In the exemplified embodiment, the socket 199 is a through-hole 150 extending through the handle portion 120 within the thumb-grip section 122 of the handle portion 120. In the exemplified embodiment, the through-hole 150 is an oval shaped aperture formed through the thumb-grip section 122 of the handle portion 120 from the front surface 124 of the handle portion 120 to the rear surface 125 of the handle portion 120. Of course, the invention is not to be so limited in all embodiments and the through-hole 150 can take on any shape as desired, such as square, rectangular, triangular or any other polygonal shape. The through-hole 150 terminates as a first opening 151 on the front surface 124 of the handle portion 120 and a second opening 152 on the rear surface 125 of the handle portion 120 opposite the front surface 124 (the second opening 152 is enclosed by the second grip component 140 in the embodiment exemplified in FIG. 4). The through-hole 150 is defined by an inner surface 155 of the handle portion 120, the inner surface 155 of the handle portion 120 forming a perimeter wall that surrounds the through-hole 150.

In certain embodiments the socket 199 may not be formed as a through-hole extending through the handle portion 120. Rather, in certain embodiments the handle portion 120 of the oral care implement 100 may comprise a socket comprising a floor. In certain embodiments, there may only be a socket on one surface of the handle, such as the front surface 124 of the handle portion 120, and the rear surface 125 of the handle portion 120 may be devoid of a socket or opening. Furthermore, in other embodiments there can be sockets on both the front and rear surfaces 124, 125 of the handle portion 120 with a floor located in between the two sockets. In embodiments that include only one socket in the handle portion 120, only one of the first and second grip components 130, 140 will be coupled to the handle portion 120. As described herein, the term socket may include both a socket having a floor as will be discussed below, and a through-hole having openings in both the front and rear surfaces 124, 125 of the handle portion 120 as has been discussed above. Thus, as used herein the term socket includes a through-hole. An embodiment whereby a socket is formed into the handle portion 120 in lieu of a complete through-hole will be discussed in more detail below with reference to FIG. 9.

The annular rim 133 of the first grip component 130 comprises an inner surface 136 that defines a central opening 138 and an outer surface 137. Similarly, the annular rim 143 of the second grip component 140 comprises an inner surface 146 that defines a central opening 148 and an outer surface 147. The first resilient body 134 of the first grip component 130 is mounted to the annular rim 133 of the first grip component 130 so as to cover the central opening 138 of the annular ring 133 of the first grip component 130. Specifically, the first resilient body 134 is molded to the inner surface 136 of the annular rim 133, the outer surface 137 of the annular rim 133 being free of the first resilient body 134. Similarly, the second resilient body 144 of the second grip component 140 is mounted to the annular rim 143 of the second grip component 140 so as to cover the central opening 148 of the annular ring 143 of the second grip component 140. Specifically, the second resilient body 144 is molded to the inner surface 146 of the annular rim 133, the outer surface 147 of the annular rim 143 being free of the second resilient body 144. Of course, in certain other embodiments the resilient bodies 134, 144 may extend onto the outer surfaces 137, 147 of the annular rims 133, 143.

As described above, the first resilient body 134 covers the central opening 138 of the annular ring 133 of the first grip component 130 and the second resilient body 144 covers the central opening 148 of the annular ring 143 of the second grip component 140. The annular rings 133, 143 are merely rings that are open on both opposing upper and lower ends thereof with a passageway (i.e., the central opening 138, 148) extending therebetween. The first and second resilient bodies 134, 144 merely covers one of the openings on one of the upper or lower ends of the respective annular rings 133, 143, thereby completely enclosing that opening. However, each of the annular rings 133, 143 remains open on its opposite end. By enclosing one of the openings on the upper or lower ends of the annular rings 133, 143, the first and second resilient bodies 134, 144 cover the central openings 138, 148. Furthermore, in the exemplified embodiment the first and second resilient bodies 134, 144 are free of penetrations to prevent air from passing therethrough.

The resilient bodies 134, 144 of each of the first and second grip components 130, 140 are formed of a resilient material, such as a thermoplastic elastomer. Furthermore, the annular rims 133, 143 of the first and second grip components 130, 140 are formed of a rigid material, such as a hard plastic. The material that forms the annular rims 133, 143 of the first and second grip components 130, 140 can be the same as the material that forms the handle portion 120 (and head portion 110) of the elongated body 101 discussed above.

However, it should be appreciated that the annular rims 133, 143 of the first and second grip components 130, 140 may not be rigid despite being formed of a rigid material due to the shape and thickness of the annular rims 133, 143. Specifically, the annular rims 133, 143 are formed of a relatively thin piece of a rigid material, which may cause the annular rims 133, 143 to have some flexibility despite being formed of a rigid material. Furthermore, in the exemplified embodiments the annular rims 133, 143 are oval in shape. However, the invention is not to be limited by the particular shape of the annular rims 133, 143, and they can take on any other polygonal or closed-geometry shape. Furthermore, in still other embodiments the annular rims 133, 143 need not form a closed-geometry. In the exemplified embodiment, the shape of the annular rims 133, 143 of the first and second grip components 130, 140 matches the shape of the through-hole 150 formed into the handle portion 120.

In the exemplified embodiment, the outer surfaces 131, 141 of the resilient bodies 134, 144 of the first and second grip components 130, 140 are dome-shaped and protrude from an upper edge 139, 149 of the respective annular rims 133, 143. Of course, the invention is not to be so limited in all embodiments and in certain other embodiments the outer surfaces 131, 141 of the resilient bodies 134, 144 of the first and second grip components 130, 140 can be flush with the upper edge 139, 149 of the annular rims 133, 143.

As discussed above, the annular rims 133, 143 are formed of a rigid material and the resilient bodies 134, 144 are formed of a resilient material. In forming the first and second grip components 130, 140, the resilient bodies 134, 144 are molded to the respective annular rims 133, 143, such as by injection molding. In the exemplified embodiment, the resilient bodies 134, 144 are molded to top portions of the annular rims 133, 143 while bottom portions of the annular rims 133, 143 remain free of the resilient bodies 134, 144. This is due to the resilient bodies 134, 144 being formed as thin resilient membranes having a thickness that is less than the height of the annular rims 133, 143 (the height of the annular rims 133, 143 extending from bottom edges 169, 179 of the annular rims 133, 143 to the upper edges 139, 149 of the annular rims 133, 143). Of course, the invention is not to be so limited in all embodiments and in certain other embodiments the resilient bodies 134, 144 may cover the entire inner surface 136, 146 of the annular rimes 133, 143. Furthermore, in certain embodiments one of the first and second grip components 130, 140 may not include an annular rim such that the resilient body of that particular grip component can be molded directly to the handle portion 120. Such an embodiment will be discussed in more detail below with reference to FIG. 7.

Figure 6:
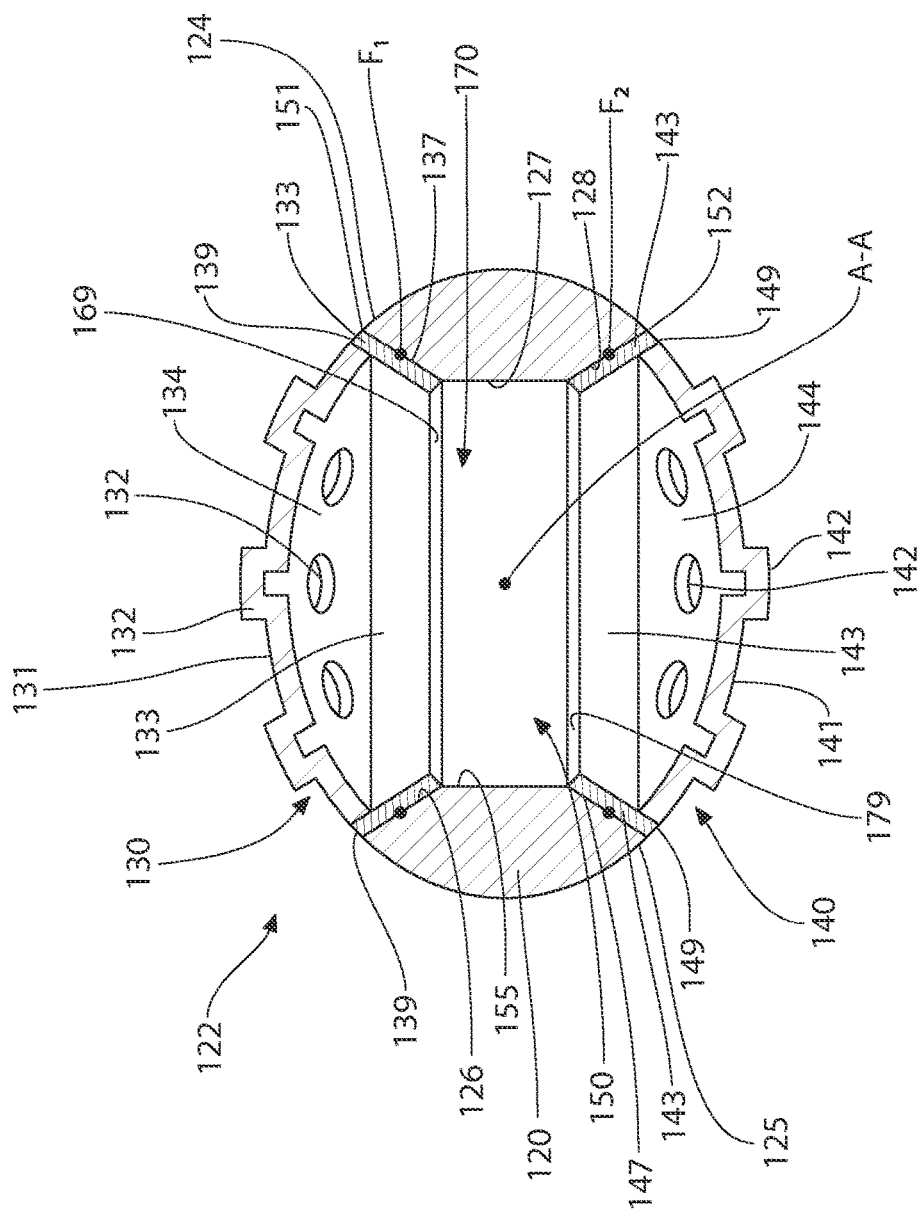
FIG. 6 is a cross-sectional view taken along line VI-VI of FIG. 3.

Referring now to FIG. 6, one embodiment of the oral care implement 100 with the first and second grip components 130, 140 coupled to the handle portion 120 is illustrated. The cross-sectional view depicted in FIG. 6 is taken along line VI-VI of FIG. 3. The first grip component 130 comprises the annular rim 133 and the first resilient body 134. The outer surface 131 of the first resilient body 134 is a dome-shaped outer surface that protrudes from the upper edge 139 of the annular rim 133. The upper edge 139 of the annular rim 133 and the dome-shaped outer surface 131 of the first resilient body 134 form a continuous, uninterrupted and smooth surface with the front surface 124 of the handle portion 120.

In the exemplified embodiment, the outer surface 137 of the annular rim 133 is tapered. Furthermore, the inner surface 155 of the handle portion 120 that defines the through-hole 150 comprises a first tapered sidewall 126, a non-tapered sidewall 127, and a second tapered sidewall 128. The first tapered sidewall 126 extends from the non-tapered sidewall 127 to the first opening 151 on the front surface 124 of the handle portion 120. The second tapered sidewall 128 extends from the non-tapered sidewall 127 to the second opening 152 on the rear surface 125 of the handle portion 120. As used herein with regard to the sidewall 155, the term tapered merely indicates that the wall is angled outwardly so that the space between opposing sides of the first tapered sidewall 126 increases as the first tapered sidewall 126 extends further from the non-tapered sidewall 127 and towards the opening 151. Similarly, the space between opposing sides of the second tapered sidewall 128 increases as the second tapered sidewall 128 extends further from the non-tapered sidewall 127 and towards the opening 152.

Of course, in certain embodiments the non-tapered sidewall 127 can be omitted and the first and second tapered sidewalls 126, 128 can be in abutting contact such that the through-hole 150 is tapered both upwardly and downwardly from a central portion of the through-hole 150 towards each of the first and second openings 151, 152. Furthermore, in certain embodiments the first and second tapered sidewalls 126, 128 can be non-tapered walls such that the inner surface 155 of the handle portion 120 is a single continuous non-tapered wall. Tapering the sidewalls 126, 128 and the annular rim 133 increases the stability of the first grip component 130 within the through-hole 150 by increasing the attachment between the annular rim 133 of the first grip component 130 and the inner surface 155 of the handle portion 120.

In the exemplified embodiment, the tapered outer surface 137 of the annular rim 133 is in abutment with the first tapered sidewall 126 of the through-hole 150. Furthermore, in the exemplified embodiment the outer surface 137 of the annular rim 133 is thermally fused at point $F_1$, such as by ultrasonic welding or otherwise, to the first tapered sidewall 126 of the through-hole 150. An annular interface is formed at the point $F_1$ between the annular rim 133 and the first tapered sidewall 126 of the through-hole 150, thereby forming a hermetic seal along the annular interface so that an air-tight pocket 170 is formed below the first resilient body 134 (in embodiments that utilize a through-hole, the air-tight pocket 170 is not formed until the second grip component 140 is also mounted to the handle portion 120). Thus, the first grip component 130 is mounted within the through-hole 150 and encloses the first opening 151 on the front surface 124 of the handle portion 120. It should be appreciated that although the first grip component 130 is described as being mounted within the through-hole 150, this includes instances in which at least a portion of the first grip component 130 is disposed within the through-hole 150 and another portion of the first grip component 130 protrudes from the through-hole 150.

As discussed above, in the exemplified embodiment the annular rim 133 of the first grip component 130 is thermally fused to the first tapered sidewall 126 of the through-hole 150. However, the invention is not to be so limited in all embodiments and in certain other embodiments mounting the first grip component 130 within the through-hole 150 can be achieved via an interference or tight fit assembly, a coupling sleeve, threaded engagement, adhesion, fasteners or the like.

The second grip component 140 comprises the annular rim 143 and the second resilient body 144. The outer surface 141 of the second resilient body 144 is a dome-shaped outer surface that protrudes from the upper edge 149 of the annular rim 143. The upper edge 149 of the annular rim 143 and the dome-shaped outer surface 141 of the second resilient body 144 form a continuous, uninterrupted and smooth surface with the rear surface 125 of the handle portion 120.

In the exemplified embodiment, the outer surface 147 of the annular rim 143 is tapered. In the exemplified embodiment, the tapered outer surface 147 of the annular rim 143 of the second grip component 140 is in abutment with the second tapered sidewall 128 of the through-hole 150. Furthermore, the outer surface 147 of the annular rim 143 of the second grip component 140 is thermally fused at point $F_2$, such as by ultrasonic welding or otherwise, to the second tapered sidewall 128 of the through-hole 150. An annular interface is formed at the point $F_2$ between the annular rim 143 and the second tapered sidewall 128 of the through-hole 150, thereby forming a hermetic seal along the annular interface so that an air-tight pocket 170 is formed in between the second resilient body 144 of the second grip component 140 and the first resilient body 134 of the first grip component. Thus, the second grip component 140 is mounted within the through-hole 150 and encloses the second opening 152 on the rear surface 125 of the handle portion 120. It should be appreciated that although the second grip component 140 is described as being mounted within the through-hole 150, this includes instances in which at least a portion of the second grip component 140 is disposed within the through-hole 150 and another portion of the second grip component 140 protrudes from the through-hole 150. In the exemplified embodiment, the first and second resilient bodies 134, 144 are free of penetrations, holes or openings therethrough, which facilitates the formation of the air-tight pocket 170 in between the first and second resilient bodies 134, 144.

As discussed above, in the exemplified embodiment the annular rim 143 of the second grip component 140 is thermally fused to the second tapered sidewall 128 of the through-hole 150. However, the invention is not to be so limited in all embodiments and in certain other embodiments mounting the second grip component 140 within the through-hole 150 can be achieved via an interference or tight fit assembly, a coupling sleeve, threaded engagement, adhesion, fasteners or the like.

In the embodiment exemplified in FIG. 6 whereby a through-hole 150 is formed into the handle portion 120 rather than a mere socket (which will be described below with reference to FIG. 9), the air-tight pocket 170 is formed in between the first grip component 130 and the second grip component 140, and even more specifically between the first resilient body 134 of the first grip component 130 and the second resilient body 144 of the second grip component 140. Thus, a free volume of space is formed between inner surfaces of the first resilient body 134 and the second resilient body 144. Each of the first and second resilient bodies 134, 144 is compressible in a direction inwardly towards the air-tight pocket 170 and towards the longitudinal axis A-A of the handle portion 120. After being compressed inwardly as described above, each of the resilient bodies 134, 144 biases back into an uncompressed state, which is the state illustrated in FIG. 6. Thus, the combination of the first and second grip components 130, 140 and the air-tight pocket 170 creates a more comfortable grip for a user during toothbrushing. Furthermore, the first and second grip components 130, 140 use less material than traditional grip components that completely fill the through-holes, thereby saving costs during manufacturing.

Figure 7:
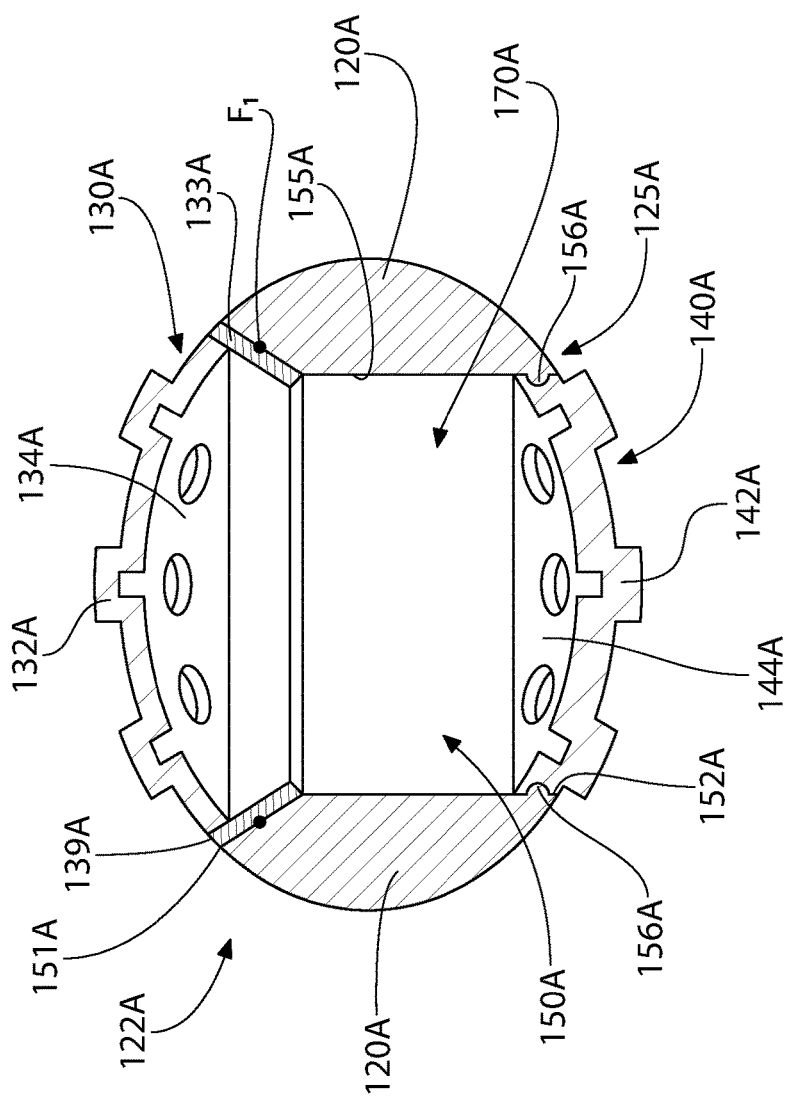
FIG. 7 is a first alternative embodiment of the cross-sectional view of FIG. 6.

Turning now to FIG. 7, an alternative embodiment of a thumb-grip section 122A of the oral care implement 100 will be described. The thumb-grip section 122A is similar to the thumb-grip section 122 described above and depicted in FIG. 6. Thus, only the structural components of the thumb-grip section 122A that are different than the thumb-grip section 122 will be discussed herein below with the understanding that the description above with regard to FIG. 6 applies to all other structural components. Furthermore, the components of the thumb-grip section 122A will have the same reference numerals as similar components from the thumb-grip section 122 except that the suffix "A" will be used. It will be understood that features that are not described below are the same as its similarly numbered feature described above. Specifically, the first grip component 130A is substantially similar to the first grip component 130 described above. Thus, a detailed description of the first grip component 130A will be not provided below, with the understanding that the description above applies.

The inner surface 155A of the handle portion 120A that defines the through-hole 150A is similar to the inner surface 155 of the handle portion 120 discussed above, except the second tapered sidewall is no longer tapered. Rather, the inner surface 155A of the handle portion 120A comprises a protuberance 156A near the second opening 152A in the rear surface 125A of the handle portion 120A. The protuberance 156A provides a mechanism for enhancing the attachment between the second grip component 140A and the handle portion 120A as will be discussed below. In the exemplified embodiment, the protuberance 156A is an annular protuberance. However, the invention is not to be so limited in all embodiments and in certain other embodiments the protuberance 156A may be one or more projections extending from the inner surface 155A of the handle portion 120A inwardly towards the through-hole 150A. Furthermore, in still other embodiments the protuberance 156A may be altogether omitted. In other embodiments, the protuberance 156A may be replaced with a recess or slot formed into the inner surface 155A of the handle portion 120A for the resilient material of the second resilient body 144A to flow into when molding the second resilient body 144A to the handle 120A.

The second grip component 140A is different from the second grip component 140 described above in that the second grip component 140A only comprises a second resilient body 144A formed of a resilient material. More specifically, the second grip component 140A does not include an annular rim, such as the annular rim 143 described above with reference to FIG. 6. The second resilient body 144A of the second grip component 140A is mounted in the through-hole 150A to enclose the second opening 152A.

Due to the lack of an annular rim, the second resilient body 144A of the second grip component 140A is mounted directly to the handle portion 120A. In the exemplified embodiment, the protuberance 156A provides a surface for the second resilient body 144A to latch onto to prevent the second resilient body 144A of the second grip component 140A from being removed from the through-hole 150A after being mounted thereto. The second resilient body 144A of the second grip component 140A is mounted to the handle portion 120A by molding the second resilient body 144A directly to the handle portion 120A, such as by injection molding. Thus, during manufacture of the toothbrush exemplified in FIG. 7, the handle portion 120A is formed with the through-hole 150A therein. Next, the handle portion 120A is positioned within a mold cavity and a resilient material, such as a thermoplastic elastomer, is injected into the mold cavity to form the second resilient body 144A. After cooling, the second resilient body 144A of the second grip component 140A is molded to the handle portion 120A to enclose the second opening 152A of the through-hole 150A.

It is not feasible to injection mold the first grip component 130A directly to the handle portion 120A after the second grip component 140A is already molded to the handle portion 120A. Thus, after the second grip component 140A is molded to the handle portion 120A, the first grip component 130A including the annular rim 133A and the first resilient body 134A can be mounted within the through-hole 150A to enclose the first opening 151A. Mounting the first grip component 130A within the through-hole 150A is achieved via thermal fusion, such as ultrasonic welding, and was described herein above with reference to FIG. 6. Once the first grip component 130A is mounted within the through-hole 150A, the air-tight pocket 170A is formed between the first and second grip components 130A, 140A.

Figure 8:
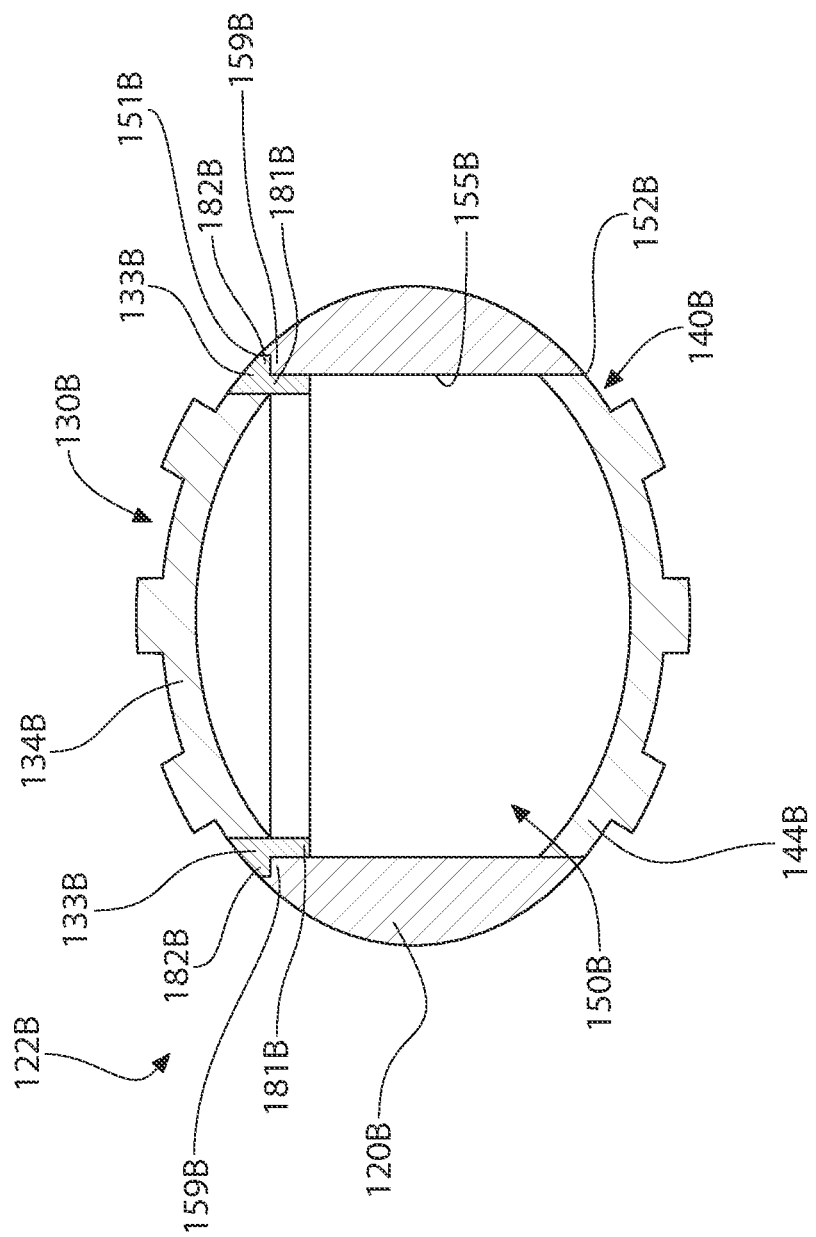
FIG. 8 is a second alternative embodiment of the cross-sectional view of FIG. 6.

Turning now to FIG. 8, a second alternative embodiment of a thumb-grip section 122B of the oral care implement 100 will be described. The thumb-grip section 122B is similar to the thumb-grip section 122A described above and depicted in FIG. 7 and the thumb-grip section 122 described above and depicted in FIG. 6. Thus, only the structural components of the thumb-grip section 122B that are different than the thumb-grip sections 122, 122A will be discussed herein below with the understanding that the description above with regard to FIGS. 6 and 7 applies to all other structural components. Furthermore, the components of the thumb-grip section 122B will have the same reference numerals as similar components from the thumb-grip sections 122, 122A except that the suffix "B" will be used. It will be understood that features that are not described below are the same as its similarly numbered feature described above.

In the embodiment exemplified in FIG. 8, the second grip component 140B is again formed only of a second resilient body 144B and is devoid of an annular rim. The second resilient body 144B of the second grip component 140B is coupled directly to the inner surface 155B of the handle portion 120B that defines the through-hole 150B. Furthermore, the inner surface 155B of the handle portion 120B does not include a protuberance, and the second resilient body 144B of the second grip component 140B is simply molded to the inner surface 155B of the handle portion 120B using techniques known to persons skilled in the art, including injection molding techniques described herein above.

The first grip component 130B comprises an annular rim 133B and a first resilient body 134B. In the exemplified embodiment, the annular rim 133B comprises a main body portion 181B and a flange 182B extending outwardly from the main body portion 181B. Furthermore, the inner surface 155B of the handle portion 120B that defines the through-hole 150B comprises a shoulder 159B. The flange/shoulder arrangement 182B, 159B is an alternative arrangement to the tapered sidewalls discussed above with regard to FIG. 6. Thus, when the first grip component 130B is mounted within the through-hole 150B, the flange 182B of the annular rim 133B is in abutment with the shoulder 159B of the inner surface 155B of the handle portion 120B. After positioning the first grip component 130B within the through-hole 150B as described above, the annular rim 133B is thermally fused to the handle portion 120B using techniques that have been described herein above.

Figure 9:
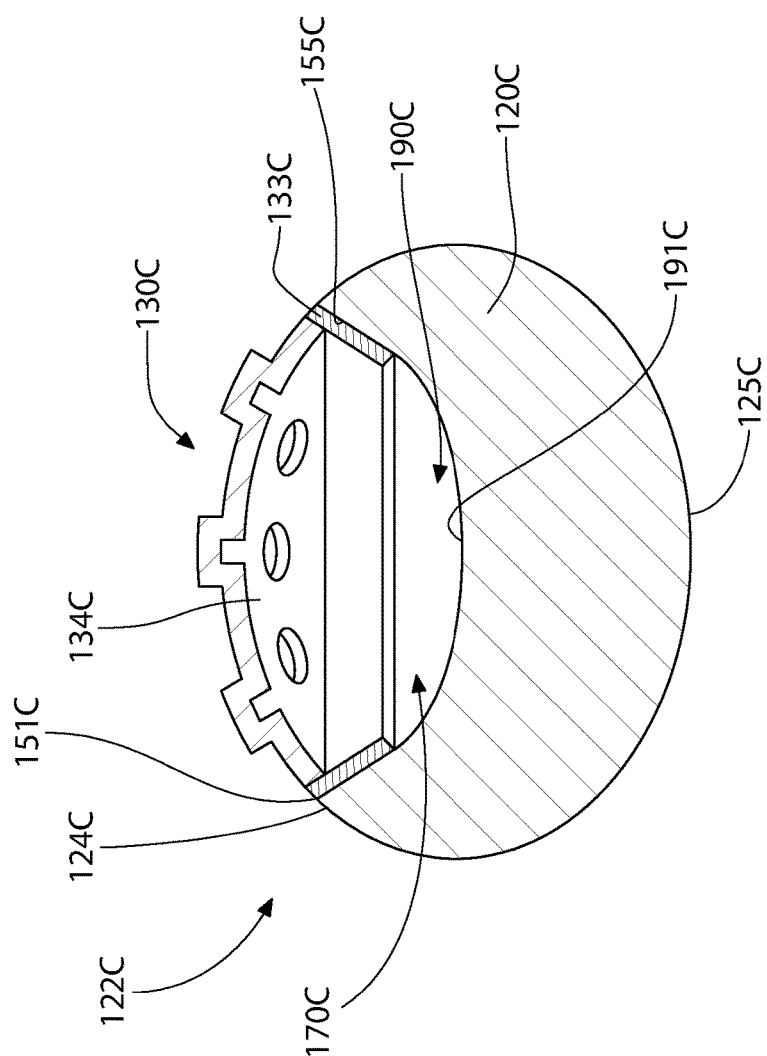
FIG. 9 is a third alternative embodiment of the cross-sectional view of FIG. 6.

Turning now to FIG. 9, a third alternative embodiment of a thumb-grip section 122C of the oral care implement 100 will be described. The thumb-grip section 122C is similar to the thumb-grip section 122A described above and depicted in FIG. 7, the thumb-grip section 122 described above and depicted in FIG. 6 and the thumb-grip section 122B described above and depicted in FIG. 8. Thus, only the structural components of the thumb-grip section 122C that are different than the thumb-grip sections 122, 122A, 122B will be discussed herein below with the understanding that the description above with regard to FIGS. 6, 7 and 8 applies to all other structural components. Furthermore, the components of the thumb-grip section 122C will have the same reference numerals as similar components from the thumb-grip sections 122, 122A, 122B except that the suffix "C" will be used. It will be understood that features that are not described below are the same as its similarly numbered feature described above.

In FIG. 9, the first grip component 130C is illustrated and comprises an annular rim 133C and a first resilient body 134B. The first grip component 130C is structurally identical to the first grip component 130 described above and illustrated in FIG. 6. The difference between the thumb-grip section 122C illustrated in FIG. 9 relative to the ones described above is in that the through-hole has been replaced with a socket 190C. The socket 190C extends from a floor 191C to an opening 151C in the front surface 124C of the handle portion 120C.

In the exemplified embodiment, there is only a single socket 190C illustrated that extends from the floor 191C to the opening 151C in the front surface 124C of the handle portion 120C. However, the invention is not to be so limited and in certain other embodiments an additional socket may be included that extends from a floor (which may be the floor 191C, or a separate floor), to an opening in the rear surface 125C of the handle portion 120C.

In the exemplified embodiment, the first grip component 130C is mounted within the socket 190C. Securing the first grip component 130C to the socket 190C can be achieved by any of the techniques discussed above, including thermal fusion of the annular rim 133C to the inner surface 155C of the handle portion 120C, tight fit assembly, interference fit and the like. Due to the relative size of the socket 190C and the first grip component 130C, an air-tight pocket 170C is formed beneath the resilient body 134C of the first grip component 130C. The resilient body 134C of the first grip component 130C is capable of being compressed in the manner that has been discussed above. Furthermore, in embodiments that utilize a second socket on the rear surface 125C of the handle portion 120C, a second grip component 130C can be mounted within such socket in a similar manner. Moreover, as has been noted above, in certain embodiments the term socket is used herein to refer to both a socket having a floor, and to refer to a through-hole, such as the through-hole 150 that has been discussed herein above.

Figure 10:
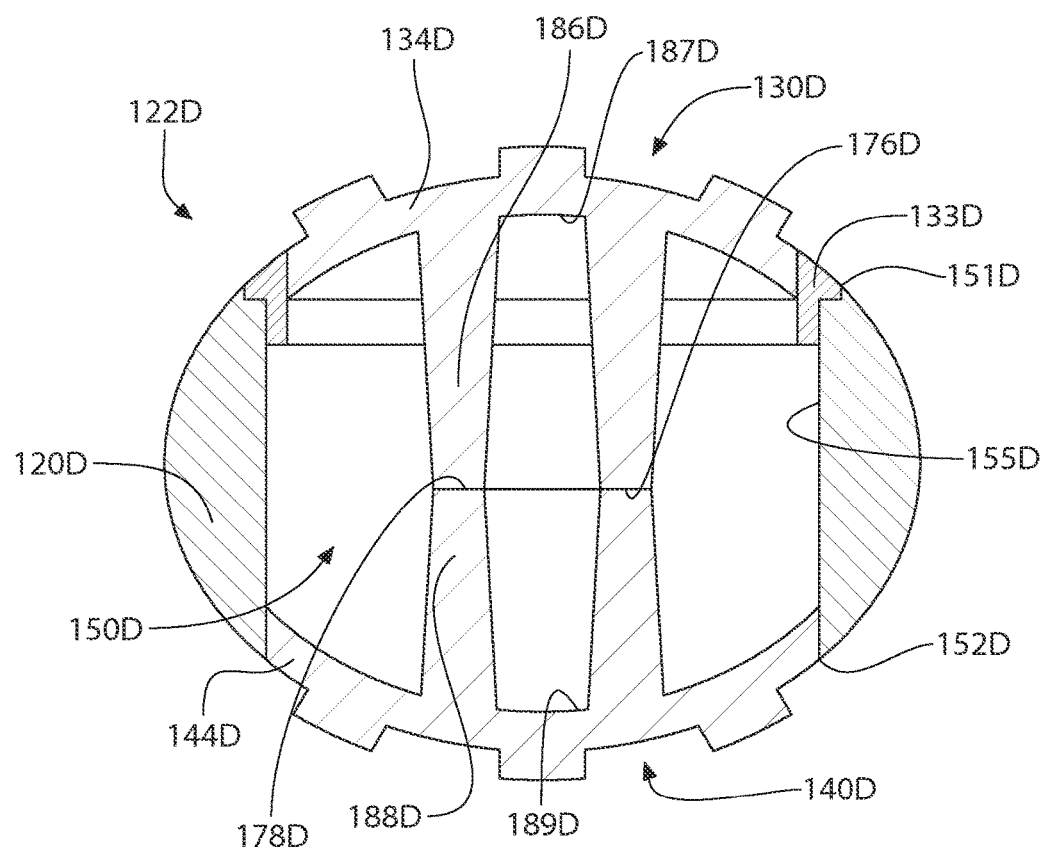
FIG. 10 is a fourth alternative embodiment of the cross-sectional view of FIG. 6.

Turning now to FIG. 10, a fourth alternative embodiment of a thumb-grip section 122D of the oral care implement 100 will be described. The thumb-grip section 122D is similar to the thumb-grip section 122B described above and depicted in FIG. 8. Thus, only the structural components of the thumb-grip section 122D that are different than the thumb-grip section 122B will be discussed herein below with the understanding that the description above with regard to FIG. 8 applies to all other structural components. Furthermore, the components of the thumb-grip section 122D will have the same reference numerals as similar components from the thumb-grip section 122B except that the suffix "D" will be used. It will be understood that features that are not described below are the same as its similarly numbered feature described above.

Although the thumb grip section 122D of FIG. 10 is illustrated whereby the first and second grip components 130D, 140D are connected to the handle portion 120D in the same manner as is depicted in FIG. 8, the invention is not to be so limited. The structural features described below with reference to FIG. 10 can be equally applied to the thumb grip sections 122 and 122A depicted in FIGS. 6 and 7.

In FIG. 10, the resilient body 134D of the first grip component 130D comprises a first projecting portion 186D extending downwardly from an inner surface 187D of the resilient body 134D into the through-hole 150D. Furthermore, the second resilient body 144D of the second grip component 140D comprises a second projecting portion 188D extending downwardly from an inner surface 189D of the second resilient body 144D into the through-hole 150D. In the exemplified embodiment, each of the first and second projecting portions 186D, 188D is an annular projection having a hollow interior. However, the invention is not to be so limited and the first and second projecting portions 186D, 188D be columnar projections wherein the interior is filled in with material rather than being hollow. Further still, each of the first and second projecting portions 186D, 188D can take on any other shape as desired.

In the exemplified embodiment, the first projecting portion 186D is formed integrally with the resilient body 134D and the second projecting portion 188D is formed integrally with the second resilient body 144D. However, the invention is not to be so limited and the first and second projecting portions 186D, 188D can be separately formed from the resilient bodies 134D, 144D and later connected thereto. In such embodiments, the first and second projecting portions 186D, 188D can be formed out of a rigid material such as a hard plastic rather than a resilient material such as a thermoplastic elastomer.

FIG. 10 illustrates the resilient bodies 134D, 144D in the biased uncompressed state. Furthermore, in the exemplified embodiment a bottom surface 176D of the first projecting portion 186D is in surface contact with a bottom surface 178D of the second projecting portion 188D while the resilient bodies 134D, 144D are in the biased uncompressed state. As a result, when a user grips the thumb-grip section 122D and applies pressure onto the resilient body 134D, that pressure will be felt by the user at the second resilient body 144D. Specifically, any movement of the resilient body 134D will be translated to the second resilient body 144D through the first and second projecting portions 186D, 188D. The first and second projecting portions 186D, 188D are in contact with each other within the free volume of space that that separates the inner surfaces 187D, 189D of the resilient bodies 134D, 144D from one another.

In other embodiments, the bottom surfaces 176D, 178D of the first and second projecting portions 186D, 188D may be spaced apart from one another when the resilient bodies 134D, 144D are in the uncompressed state. Upon the application of a compression force onto one of the resilient bodies 134D, 144D, the bottom surfaces 176D, 178D will contact one another to generate a tactile sensation to the user. Thus, the first and second projecting portions 186D, 188D can be utilized to present the user with a tactile sensation that can either provide a desired massaging effect to the user, or can serve as a warning that the user is gripping the oral care implement with excessive force.

Figure 11:
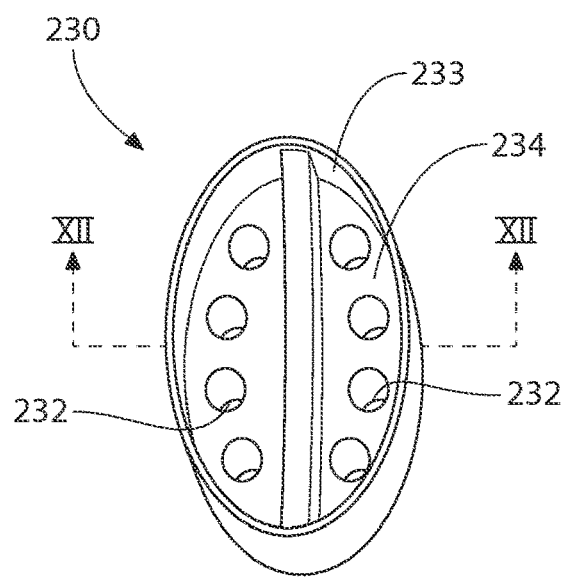
FIG. 11 is a perspective view of a gripping component with a strut according to an embodiment of the present invention.
Figure 12:
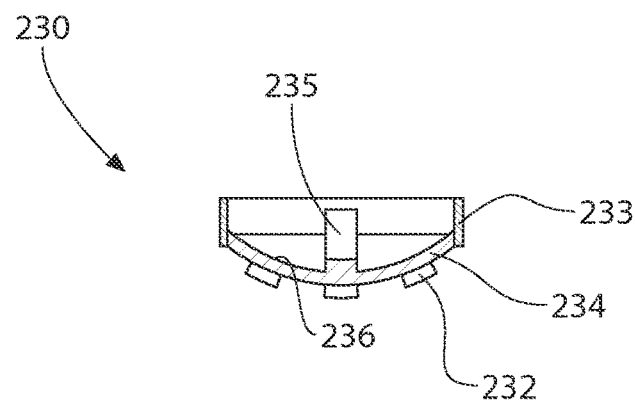
FIG. 12 is a cross-sectional view taken along line XII-XII of FIG. 11

Referring now to FIGS. 11 and 12 concurrently, an alternative embodiment of a grip component 230 is illustrated. The grip component 230 comprises an annular rim 233 and a resilient body 234. The resilient body 234 comprises a plurality of protuberances 232 protruding therefrom. Thus, the grip component 230 is similar to the first and second grip components 130, 140 discussed above with reference to FIGS. 1-6. However, the grip component 230 further comprises a strut 235 extending from a first side of the annular rim 233 to a second side of the annular rim 233 opposite the first side. In the exemplified embodiment, the strut 235 is formed integrally with the resilient body 234 out of the resilient material. The strut 235 provides additional strength and rigidity to the resilient body 234, and provides strength against compression of the resilient body 234.

In certain other embodiments, the strut 235 can be formed integrally with the annular rim 233 out of a rigid material, such as one of the hard plastic materials discussed above. In such embodiments, the strut 235 is located adjacent to a bottom surface 236 of the resilient body 234. However, the invention is not to be so limited in all embodiments and in certain embodiments the strut 235 is embedded within the resilient body 234 after the resilient body 234 is molded to the annular rim 233 (see FIG. 14). Thus, the strut 235 can be formed integrally with the annular rim 233 of the grip component 230 or integrally with the resilient body 234 of the grip component 230.

In certain embodiments that utilize the strut 235, the resilient body 234 may comprise one or more apertures forming passageways to a space beneath the resilient body 234. In such embodiments, there is no air-tight pocket formed beneath the resilient body 234. Thus, in such embodiments rather than having the air-tight pocket provide sufficient pressure against the resilient body 234 to facilitate the resilient body 234 maintaining its shape, the strut 235 will achieve the same effect. Furthermore, such factors as material stiffness, thickness and overall geometry of the resilient body 234 can adjust the structure and resiliency of the resilient body 234 to achieve a desired effect. Moreover, apertures can be formed into the resilient body 234 in embodiments that do not utilize a strut as desired in order to provide holes for the ingress and egress of air into and out of the air pocket.

Figure 13:
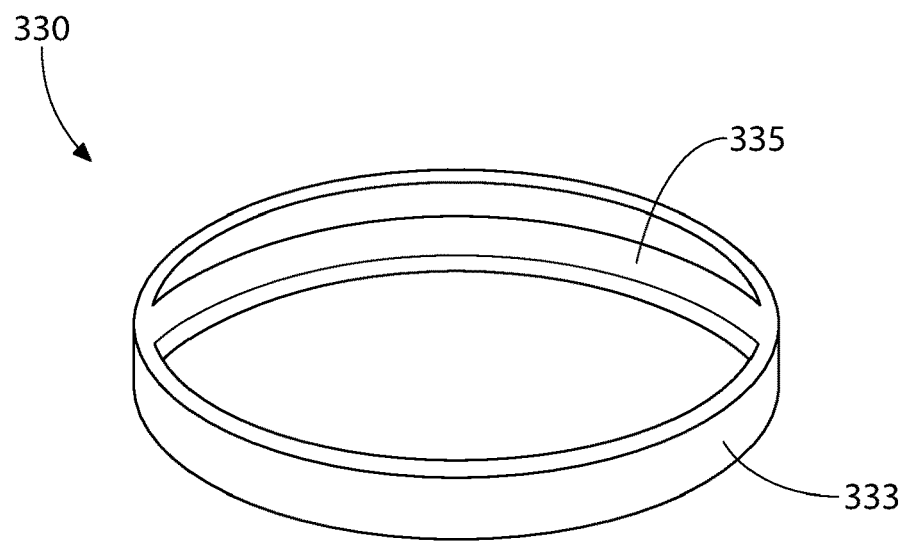
FIG. 13 is a perspective view of a gripping component having an annular rim and a strut according to an alternative embodiment of the present invention.
Figure 14:
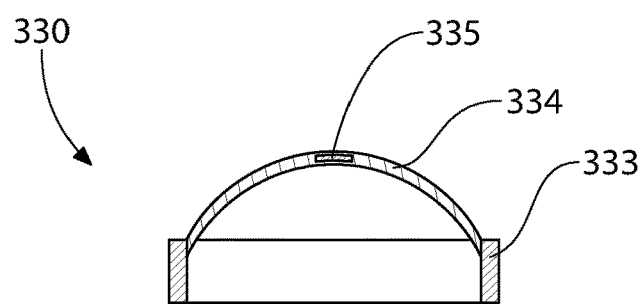
FIG. 14 is a cross-sectional schematic of the gripping component of FIG. 13 with a resilient body molded to the annular rim.
Figure 15:
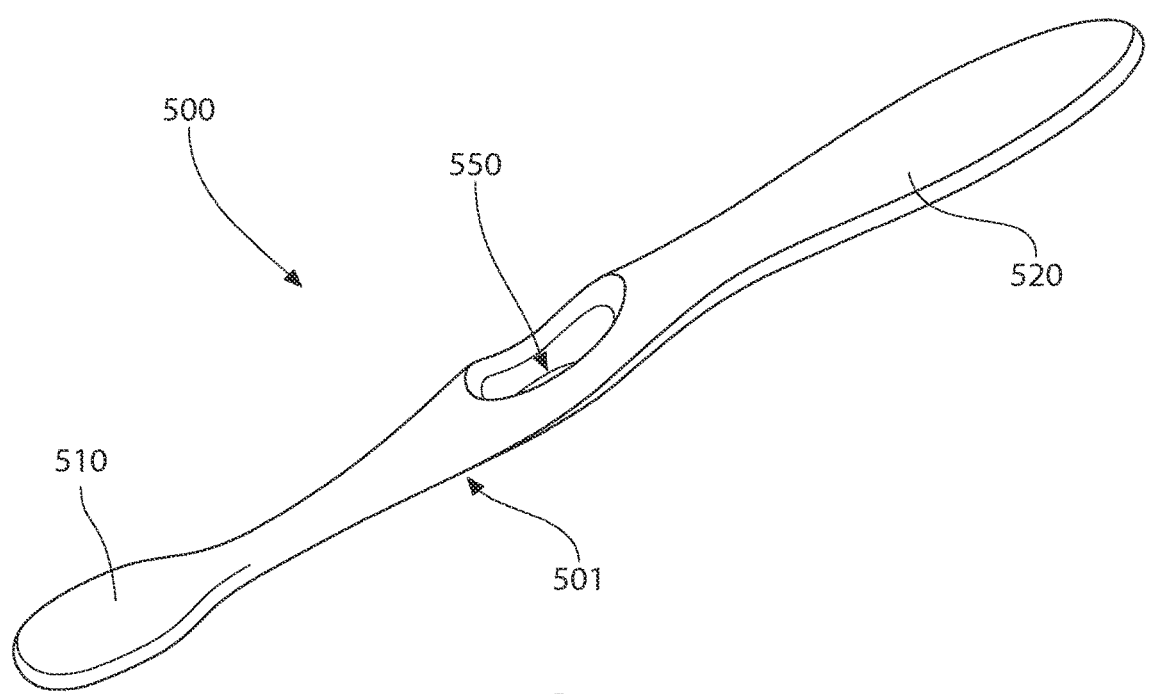
FIG. 15 is a perspective view of an elongated body of an oral care implement in accordance with an embodiment of the present invention.
Figure 16:
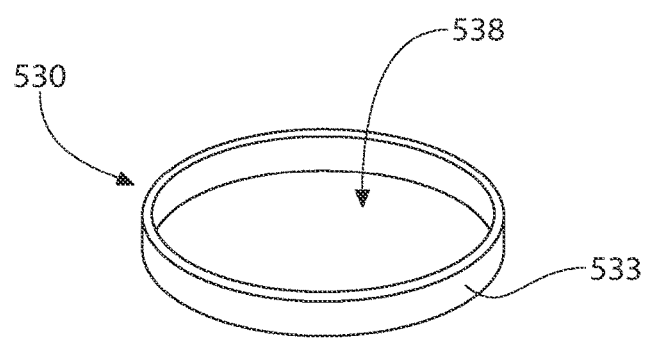
FIG. 16 is a perspective view of an annular rim of a grip component in accordance with an embodiment of the present invention.

Referring to FIGS. 13 and 14, an alternative embodiment of a grip component 330 will be briefly described. FIG. 13 illustrates the annular rim 333 of the grip component 330 having a strut 335 extending from one end of the annular rim 333 to another opposite end of the annular rim 333. In the embodiment exemplified in FIGS. 13 and 14, the strut 335 is formed integrally with the annular rim 333. FIG. 14 illustrates a cross-sectional view of the annular rim 333 of the grip component 330 having a resilient body 334 molded thereon. The grip component 330 is similar to the grip component 230 discussed above except that the resilient body 334 of the grip component 330 does not have protuberances extending therefrom. Furthermore, the strut 335 is embedded within the resilient material of the resilient body 334.

In the exemplified embodiment, the oral care implement is illustrated and described with one socket and/or through-hole located on the handle portion of the oral care implement. However, the invention is not to be so limited in all embodiments and in certain other embodiments the oral care implement may include a plurality of sockets and/or through-holes located on the handle portion of the oral care implement. In such embodiments, each of the through-holes is closed by a grip component that is mounted to the handle portion utilizing the techniques that have been described above, and the methods that will be described in more detail below.

Referring now to FIGS. 15-18 concurrently, a method of manufacturing an oral care implement 500 having the features discussed herein will be described. In manufacturing the oral care implement 500, first an elongated body 501 comprising a handle portion 520 and a head portion 510 is formed from a first material, the first material being a hard plastic. The elongated body 501 is formed so as to have a socket 550 formed into the handle portion 520. Forming the elongated body 501 includes forming a first mold cavity and injecting a molten form of the first material into the first mold cavity, the first mold cavity having a shape that corresponds to the shape of the elongated body 501. After injecting the molten form of the first material into the first mold cavity, the molten form of the first material is allowed to cool within the first mold cavity, thereby forming the elongated body 501 having the socket 550 formed therein.

Next, a first grip component 530 is formed comprising an annular rim 533 having a central opening 538 and a first resilient body 534. The annular rim 533 is formed of a second material. In certain embodiments, the first material that forms the elongated body 501 is the same as the second material that forms the annular rim 533. However, the invention is not to be so limited in all embodiments. Nonetheless, it is preferable that both the first and second materials are rigid materials.

Figure 17:
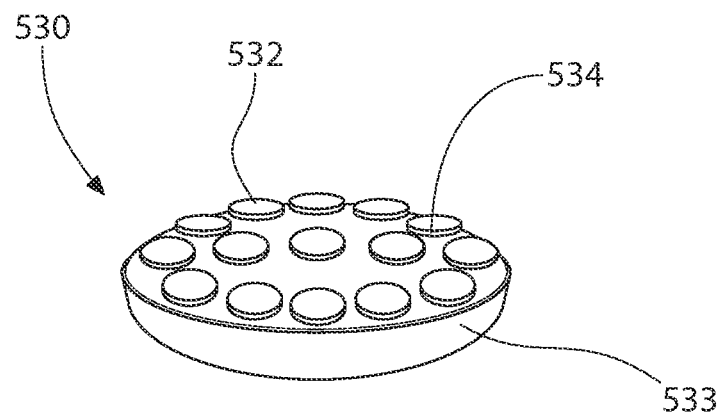
FIG. 17 is a perspective view of a grip component in accordance with an embodiment of the present invention.
Figure 18:
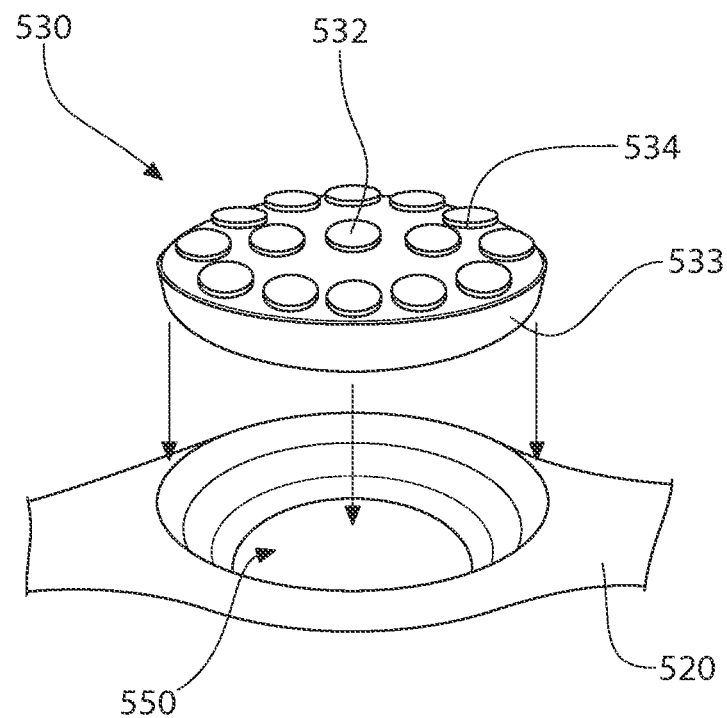
FIG. 18 is a perspective view illustrating mounting the grip component of FIG. 17 into a socket of a handle of an oral care implement.

Forming the annular rim 533 includes forming a second mold cavity and injecting a molten form of the second material into the second mold cavity, the second mold cavity having a shape that corresponds to the shape of the annular rim 533. Next, the molten form of the second material within the second mold is allowed to cool, thereby forming the annular rim 533. After forming the annular rim 533, the first resilient body 534 is mounted to the annular rim 533 so as to cover the opening 538 in the annular ring 533. The first resilient body 534 is formed of a third material. In certain embodiments, the third material is more resilient than the first and second materials, and more specifically the third material can be a thermoplastic elastomer. To form the first resilient body 534 and mold the first resilient body 534 onto the annular ring 533, a third mold cavity is formed at the central opening 538 of the annular rim 533 and a molten form of the third material is injected into the third mold cavity into contact with the annular rim 533. The third mold cavity has a shape that corresponds to the first resilient body 534, including any protuberances 532 that are extending from the first resilient body 534. Finally, the molten form of the third material is allowed to cool within the third mold cavity, thereby forming the first grip component 530 in which the first resilient body 534 is molded to the annular rim 533. In the exemplified embodiments, the first and second materials are rigid materials and the third material is a resilient material. FIG. 17 illustrates the first grip component 530 having the first resilient body 534 molded onto the annular rim 533.

After forming the elongated body 501 and the first grip component 530, the first grip component 530 is mounted within the socket 550 of the handle portion 520 of the elongated body 501. This includes positioning the first grip component 530 within the socket of the handle portion 520 and thermally fusing the annular rim 533 of the grip component 530 to the handle portion 520, thereby securing the first grip component 530 to the handle portion 520. Of course, as has been discussed above the first grip component 530 may otherwise be secured to the handle portion 520, such as be utilizing an interference fit, adhesion, fasteners or the like.

In certain embodiments as discussed above, the socket 550 is a through-hole terminating as a first opening on a first side of the handle portion 520 and terminating as a second opening on a second side of the handle portion 520, the second side being opposite the first side (such as in an embodiment whereby the first side of the handle portion 520 is the front surface of the handle portion 520 and the second side of the handle portion 520 is the rear surface of the handle portion 520). In such an embodiment, prior to mounting the first grip component 530 including the annular rim 533 and the resilient body 534 to the handle portion 520, a second grip component is mounted to the handle portion 520.

In certain embodiments, the second grip component comprises a second resilient body formed of a fourth material, the fourth material being a resilient material. The second grip component is formed by creating a fourth mold cavity at the second opening of the through-hole 550 of the handle portion 520 and injecting a molten form of the fourth material into the fourth mold cavity and in contact with the handle portion 520. The fourth mold cavity has a shape that corresponds to the shape of the second grip component. Next, the molten form of the fourth material is allowed to cool within the fourth mold cavity, thereby forming the second grip component. Of course, the invention is not to be so limited and in certain embodiments the second grip component may comprise both the resilient body and an annular rim, and the second grip component may be formed and attached to the handle portion 520 in the same manner as discussed above with regard to the first grip component 530.

After molding the second grip component to the handle portion 520 to enclose the second opening, the first grip component 530 including the annular rim 533 and the resilient body 534 is mounted to the handle portion 520 to close the first opening on the first side of the handle portion 520. After the second grip component is molded to the handle portion 520 to enclose the second opening and the first grip component 530 is mounted to the handle portion 520 so as to enclose the first opening, an air-tight pocket is formed beneath the first resilient body 534, and more specifically in between the first resilient body 534 of the first grip component 530 and the second resilient body of the second grip component.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
   an elongated body comprising a head portion and a handle portion, the handle portion comprising a socket;
   at least one tooth cleaning element mounted to the head portion of the elongated body; and
   a first grip component comprising:
      an annular rim defining a central opening, the annular rim formed of a rigid material; and
      a resilient body mounted to the annular rim that covers the central opening, the resilient body formed of a resilient material;
   the first grip component mounted within the socket; and
   wherein the resilient body comprises a dome shaped outer surface protruding from an upper edge of the annular rim, the upper edge of the annular rim and the dome-shaped outer surface of the resilient body forming a continuous, uninterrupted and smooth surface with an outer surface of the handle portion.

2. The oral care implement according to claim 1 wherein the handle portion is formed of a rigid material, the annular rim thermally fused to the handle portion.

3. The oral care implement according to claim 1 wherein an annular interface is formed between the annular rim and the handle portion, and wherein a hermetic seal is formed along the annular interface so that an air-tight pocket is formed below the resilient body.

4. The oral care implement according to claim 1 wherein the resilient body is molded to the annular rim.

5. The oral care implement according to claim 1 wherein the resilient body further comprises a plurality of protuberances protruding from the dome-shaped outer surface.

6. The oral care implement according to claim 1 wherein the handle portion comprises a neck section, a thumb-grip section and a finger grip section, the thumb-grip section located between the neck section and the finger grip section, the socket located within the thumb-grip section.

7. The oral care implement according to claim 1 wherein the socket is a through-hole extending through the handle portion, the through hole terminating as a first opening on a first side of the handle portion and terminating as a second opening on a second side of the handle portion opposite the first side, the first grip component mounted within the through-hole to enclose the first opening.

8. The oral care implement according to claim 7 further comprising a second grip component mounted within the through-hole to enclose the second opening, the second grip component comprises a second resilient body formed of a resilient material.

9. The oral care implement according to claim 8 wherein the second resilient body of the second grip component is molded directly to the handle portion.

10. The oral care implement according to claim 8 wherein the second grip component comprises an annular rim formed of a rigid material, the second resilient body of the second grip component molded to the annular rim of the second grip component, the annular rim of the second grip component thermally fused to the handle portion.

11. The oral care implement according to claim 9 wherein an air-tight pocket is formed between the first and second grip components.

12. The oral care implement according to claim 8 wherein the resilient body of the first grip component comprises a first projecting portion extending from an inner surface of the resilient body into the through-hole, and wherein the second resilient body of the second grip component comprises a second projecting portion extending from an inner surface of the second resilient body into the through-hole.

13. The oral care implement according to claim 12 wherein the first projecting portion of the first resilient body is in contact with the second projecting portion of the second resilient body.

14. The oral care implement according to claim 1 wherein the resilient body of the first grip component is compressible in a direction towards a longitudinal axis of the handle portion and biases back to an uncompressed state.

15. The oral care implement according to claim 1 wherein the annular rim of the first grip component comprises a tapered outer surface, the socket comprising a section having a tapered sidewall, the tapered outer surface of the annular rim in abutment with the tapered sidewall.

16. The oral care implement according to claim 1 wherein the resilient body of the first grip component comprises one or more apertures, the one or more apertures forming passageways to a space beneath the resilient body.

17. The oral care implement according to claim 1 wherein the annular rim of the first grip component further comprises a strut extending from a first side of the annular rim to a second side of the annular rim opposite the first side of the annular rim.

18. An oral care implement comprising:
a head having at least one tooth cleaning element;
a handle coupled to the head, the handle comprising at least one through-hole extending through the handle, the through-hole terminating as a first opening on a first side of the handle and terminating as a second opening on a second side of the handle;
a first grip component coupled to the handle to enclose the first opening, the first grip component comprising an annular rim defining a central opening and a first resilient body mounted to the annular rim that covers the central opening, the annular rim formed of a rigid first material and the first resilient body formed of a resilient second material, wherein the resilient material of the first resilient body comprises a dome shaped outer surface protruding from an upper edge of the annular rim, the upper edge of the annular rim and the dome shaped outer surface of the resilient body forming a continuous, uninterrupted and smooth surface with an outer surface of the handle; and
a second grip component coupled to the handle to enclose the second opening, the second grip component comprises a second resilient body formed of a third material;
wherein the first resilient body comprises a first projecting portion extending from an inner surface of the first resilient body into the through-hole, wherein the second resilient body comprises a second projecting portion extending from an inner surface of the second resilient body into the through-hole, wherein the first projecting portion of the first resilient body is in contact with the second projecting portion of the second resilient body, and wherein the inner surface of the first resilient body and the inner surface of the second resilient body are spaced apart so that a cavity is formed between the first and second resilient bodies.

19. The oral care implement according to claim 18 wherein the cavity is air-filled.

20. The oral care implement according to claim 18 wherein the first resilient body is molded to the annular rim and the annular rim is thermally fused to the handle.

* * * * *